United States Patent [19]
Bryne

[11] 4,116,199
[45] Sep. 26, 1978

[54] CRYOSURGICAL INSTRUMENT RESERVOIR

[75] Inventor: Michael D. Bryne, Vernon, Conn.

[73] Assignee: Brymill Corporation, Vernon, Conn.

[21] Appl. No.: 747,904

[22] Filed: Dec. 6, 1976

[51] Int. Cl.$^2$ .............................................. A61B 17/36
[52] U.S. Cl. ................................ 128/303.1; 215/13 R; 220/901
[58] Field of Search ...................... 128/303.1; 220/9 C, 220/9 LG; 215/13 R, 31

[56] References Cited

U.S. PATENT DOCUMENTS

| | | | |
|---|---|---|---|
| 1,511,852 | 10/1924 | Wagner | 220/9 C |
| 2,645,097 | 11/1950 | Posch | 128/303.1 |
| 3,739,956 | 6/1973 | Reynolds | 128/303.1 |
| 3,823,718 | 7/1974 | Tromovitch | 128/303.1 |
| 3,863,794 | 2/1975 | Hata | 220/9 C |
| 3,889,681 | 6/1975 | Waller et al. | 128/303.1 |

FOREIGN PATENT DOCUMENTS

| | | | |
|---|---|---|---|
| 1,122,590 | 5/1956 | France | 220/9 C |
| 1,459,414 | 11/1966 | France | 220/9 C |

*Primary Examiner*—Robert W. Michell
*Assistant Examiner*—Arthur S. Rose
*Attorney, Agent, or Firm*—M. P. Williams

[57] ABSTRACT

A cryosurgical instrument employing a standard, doublewalled, metal vacuum bottle or dewer has a collar metallurgically bonded to the top of the dewer near the mouth thereof to provide machined threads for releasably engaging the delivery and control portion of the instrument to the reservoir portion of the instrument. The collar provides additional strength and support to the portion where the two walls of the dewer are joined to each other. A vent is provided in a bottom cap of the vacuum dewer. A valve directly in the cryogen delivery line is connected by a stem to a fulcrumed operating handle (the subject of a division thereof); a 360° fulcrum is used, to permit rotating the handle for thumb or finger operation with either the right or the left hand, as desired; rotation of the handle also rotates the valve stem so as to assist in freeing it from crystalline adhesion which may result from moisture in the cryogen or in the ambient air. In one embodiment, the 360° fulcrum has a cam surface which can be positioned wherever it is desired to cause the operating handle to be locked into the on position, regardless of its position of rotation. The fulcrum is adjustable for the relationship between the motion of the handle and the operation of the valve.

3 Claims, 2 Drawing Figures

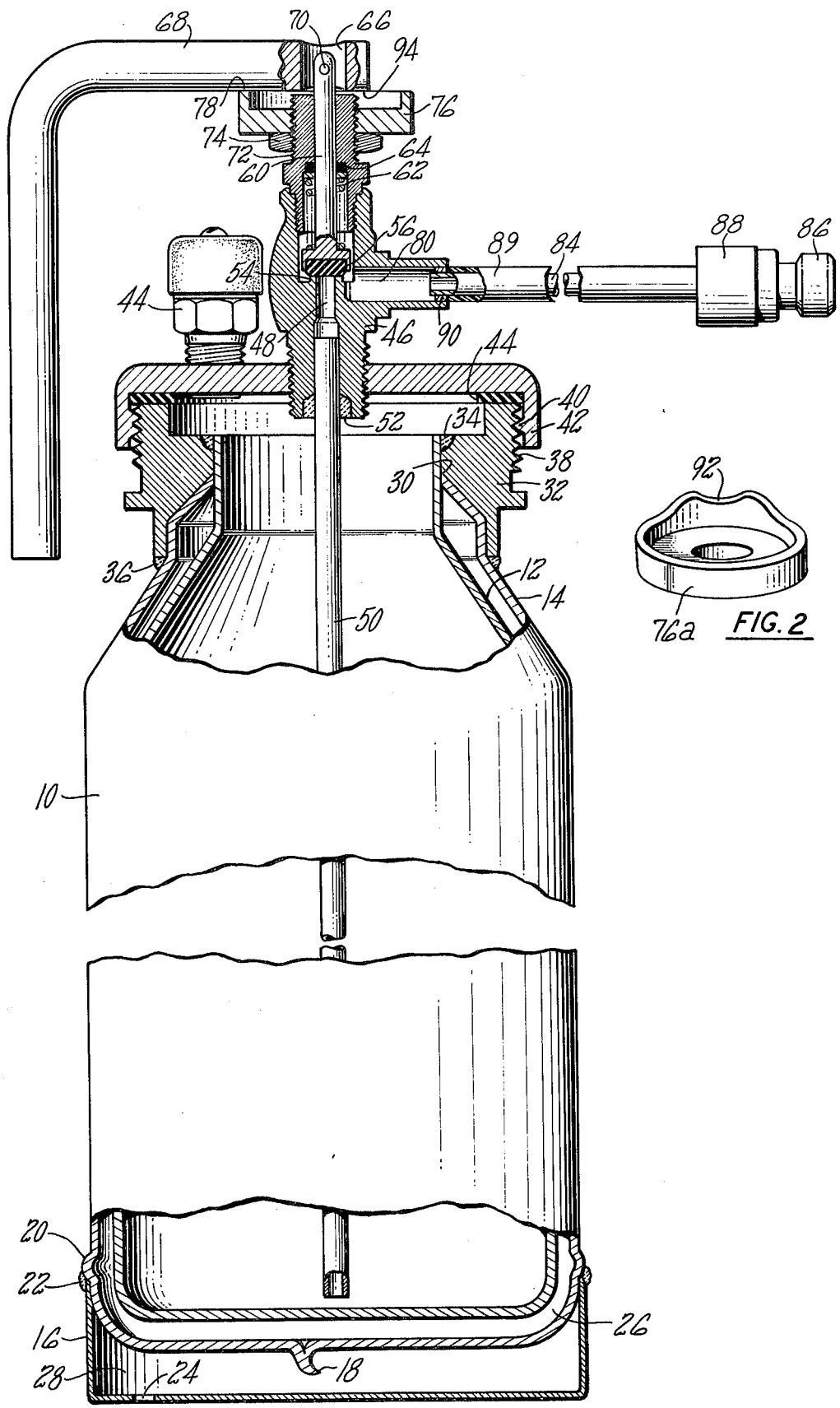

CRYOSURGICAL INSTRUMENT RESERVOIR

BACKGROUND OF THE INVENTION

1. Field of the Invention

This invention relates to cryosurgical instruments, and more particularly to vacuum reservoir cryosurgical instruments.

2. Description of the Prior Art

The first hand held cryosurgical instrument for general surgical use is set forth in my U.S. Pat. No. 3,534,739. That instrument controlled the venting of continuously, self-boiling cryogen in order to force the delivery of liquid cryogen as desired. Since the device is continuously vented, except against the pressure induced by the operator in manipulating the vent closing valve thereof, no pressure relief was necessary, and none of the liquid cryogen flowed through the valve. As clinical history developed in the years following the introduction of this hand held cryosurgical unit, more and more usage was found therefore.

In attempts to provide lower cost cryosurgical units which would utilize the liquid cryogen more economically by reducing the rate of boiling thereof while in the reservoir of a cryosurgical instrument, standard, commercial vacuum bottles having dual metallic walls have been used as the basis for construction of cryosurgical instruments. These devices, it has been found, have numerous drawbacks. First of all, since the intent is to conserve nitrogen, the devices were not provided with normally open vents, the closing of which would force liquid through the delivery tube, but rather were provided with valves directly in the cryogen delivery tube, with pressure relief valves to avoid the buildup of excess pressure therein. This, in turn, causes the units to be normally operated at some nominal pressure (such as 10 or 15 psi) which means that the unit is quiescently under pressure even when not being used so long as there is cryogen in the reservoir. Additionally, the rupture or breach of the internal wall of the vacuum bottle has been found to allow cryogen to leak into the normally evacuated space between the walls, causing it to vaporize and expand. Typically, these vacuum bottles have pinched tubes at the bases thereof through which the vacuum is pulled prior to sealing them off. Normally, the pinched tube is open whenever the interwall space is pressurized by cryogen. Naturally, this type of problem is one which is not normally faced in the manufacture of commercial vacuum bottles for ordinary domestic use. An additional problem is that should the pinched tube not prove to be the weakest point in the interwall cavity, the chances are that the joint between the two walls near the mouth of the bottle will be the weakest point. Should this joint rupture while the instrument is in use, it could cause the control and delivery portion of the device to be explosively expelled from the reservoir, and could even cause direct spraying of liquid or gaseous cryogen on the user or the patient being treated.

SUMMARY OF THE INVENTION

Objects of the present invention include improvements in hand held, vacuum reservoir cryosurgical instruments.

According to the invention, a low cost, double metal wall vacuum bottle is rendered safe for use with a liquefied cryogen by provision of a heavy collar at the top thereof which encompasses the joint between the two metal walls, and by provision of a vent hole in the bottom pan that protects the vacuum seal thereof. According further to the present invention, the collar is provided with machined threads to permit joining the vacuum bottle reservoir to the control and delivery portion of the instrument in a sure and safe manner.

The present invention permits manufacture of a highly reliable and safe, as well as versatile, cryosurgical instrument utilizing mainly standard components which are widely available in the art. The invention permits cryosurgical use of standard, commercial vacuum bottles without incurring danger of violent rupture or explosion as a consequence of the extreme cold which the unit must withstand, and the highly volatile nature of liquefied gas cryogens.

The foregoing and other objects, features and advantages of the present invention should become more apparent in the light of the following detailed description of a preferred embodiment thereof, as illustrated in the accompanying drawing.

BRIEF DESCRIPTION OF THE DRAWING

FIG. 1 is a partially sectioned side elevation view of a preferred embodiment of the invention; and FIG. 2 is a perspective view of an alternative embodiment of a fulcrum which may be used in the embodiment of FIG. 1.

DESCRIPTION OF THE PREFERRED EMBODIMENTS

Referring now to FIG. 1, the reservoir of a cryosurgical instrument in accordance with the present invention comprises a standard commercial vacuum bottle 10 which consists mainly of an inner wall 12, an outer wall 14 and a bottom pan 16. The bottom pan protects a vacuum seal such as a pinch tube 18 which is used to evacuate the bottle and then sealed off in a fashion known to the art. To support the pan 16, the outer wall may have an annular crease 20 formed therein, and the pan may be suitably bonded to the outer wall such as by brazing or welding 22. In accordance with one aspect of the present invention, a hole 24 is provided in the pan 16 so that in the event that the inner wall 12 is ruptured, allowing cryogen to flow into the normally-evacuated void 26 between the two walls 12, 14, the danger of the vacuum seal opening and allowing gaseous pressure to build up in the void 28 within the pan 16 is eliminated. Therefore, the present invention overcomes the danger of a pressure buildup which could cause the pan 16 to be violently expelled from the reservoir and cause injury.

At the top of the vacuum bottle 10, the walls 12, 14 are normally joined by brazing or welding 30. Typically, the final, upper portion of the outer wall 14 may have rolled or stamped threads therein to receive a drinking cup, in a fashion well known in the art (although these are not shown herein for simplicity). According to another aspect of the invention, the joint 30 is protected against rupture by the buildup of pressure between the walls 12, 14 which might result if there is a breach in the inner wall while the vacuum bottle is containing cryogen, by means of a heavy metal collar 32 which is metallurgically bonded as at 34 and 36 so as to form a strong unitary structure. The collar 32 is at least several times thicker than the walls 12, 14. The collar 32 is also provided with machined threads 38 in order to facilitate releasable joinder with similar threads 40 of a cap 42 which forms the basic foundation structure of the control and delivery portion of the instrument. The cap 42 is sealed to the collar 32 by a silicone gasket 44.

The machined threads 38, 40 permit removal of the cap 42 for filling of the unit, while at the same time preventing the cap 42 from inadvertently being sprung from the collar 32 as from dropping or from excessive pressure. The cap 42 is drilled and tapped so as to receive a standard pressure relief valve 44 that limits the buildup of pressure within the instrument to a desired amount, which may be on the order of 10 or 15 psi. The cap is also drilled and tapped so as to receive a valve structure 46 which includes a central bore 48 that receives a hollow tube 50 which is brazed or otherwise bonded (as at 52) to the valve member 46. The valve has an annular seat 54 which cooperates with a silicone valve pad 56 mounted in a valve stem 60. The valve stem 60 is normally forced downwardly as seen in FIG. 1 so as to cause closure of the valve by means of a spring 62. The valve stem 60 is sealed by a silicone O-ring 64. The top of the valve stem fits within an oval or elongated hole 66 within a handle 68 and is rotatably fixed thereto by means of a pin 70. The handle 68 may simply comprise a bent metal rod. The top of the valve member 46 is provided with threads 72 which receive an adjusting nut 74 that controls the amount of play (vertically as seen in FIG. 1) of a dish like structure which provides an annular fulcrum 76. When the handle 68 is rocked counterclockwise (as seen in FIG. 1) about the pin 70, its surface 78 will contact the upper surface of the fulcrum 76 causing the pin 70 and therefore the valve stem 60 to be raised, thereby opening the valve. Since the valve stem 60 is fully rotatable within the valve member 46, and since the fulcrum 76 is annular in shape, the handle 68 and valve stem 60 may be rotated in any desired position about the axis of the valve stem 60 and still be fully operable. Rotation of the handle 68 about the axis of the valve stem 60 will also cause rotation of the valve pad 56 and tend to free it when it may have adhered by ice to the valve seat 54. Similarly, should moisture cause freezing of the valve stem 60 to the O-ring 64, rotation of the handle about the valve stem axis will shear the ice and free the device from being stuck in an open position. When the valve stem 60 is in the upward position as a result of movement of the handle 68, the cryogen can flow up the tube 50 through the central bore 48 and into a lateral bore 80. Into the bore 80 there is fitted a tube 84 which is of somewhat smaller diameter than the bore 80. The reason for this is to facilitate a certain amount of vaporization of the liquefied gas cryogen prior to its reaching an orifice 86 which may be joined to the tube 84 by a standard fitting 88 in the fashion described in my aforementioned patent. This gasification results from the fact that the cap 42, the valve member 46, even the pressure relief valve 44, the fulcrum 76 and the handle 68 may all be heat conducting metal, thereby accepting heat from the ambient which can be given off to the cryogen within the bore 80 thereby tending to gasify it; by having the tube 84 of a somewhat smaller diameter, the amount of liquid which may reside in the tube 84 during operation is limited, thereby limiting the cooling rate just prior to delivery to a rate which is substantially low with respect to the natural flow of heat into the instrument to permit a certain amount of gasification of the cryogen to result. As an example, the structure shown in FIG. 1 may provide at its orifice 86 cryogen of roughly an equal mixture of gas and liquid, perhaps predominantly gas. In order to facilitate joinder of the smaller tube 84 within the larger bore 80, a metal washer filler 90 may be bonded both to the valve member 46 and to the tube 84 metallurgically, such as by brazing.

Referring now to FIG. 2, an additional aspect of the disclosed embodiment includes a fulcrum 76a of a generally annular shape, but having a cam portion 92 thereon such that rotation of the cam portion 92 to a point at the surface 78 of the handle 68 will cause a surface of the handle 94 to contact the upper shoulder of the threads 72 and thereby cause the valve stem 60 to be lifted, whereby the instrument is operable in a steady state on condition.

As described, the cryosurgical instrument in accordance with the present invention is substantially all durable metal, having only a silicone valve pad and a silicone seal therein. The vacuum bottle is reinforced by the collar 32 at the point where the walls are joined, and has pressure relief provided by the vent hole 24 at the bottom to accomodate all ruptures which may leak through the vacuum seal 18. The unit provides machined, metal to metal threads, which renders the securing of the control and delivery portion to the reservoir portion adequate and safe. The inline valve is substantially freeze proof, and is additionally freeable by rotation about the longitudinal axis of the valve stem by means of the handle. The annular fulcrum allows motion of the handle in substantially any position within 350°, and also permits a lock-on type of operation with the embodiment of FIG. 2, without regard to the rotary position of the handle.

The tube 84 may be sheathed by a non-sticking plastic tubing 89, or the like, if desired. The elongated hole 66 allows free motion of the valve stem 60 therewithin without regard to the position of the adjusting nut 74. The valve structure may be modified from any of several which are of standard design in the market. The reservoir herein may be used with other valves and pressure controls than those disclosed herein.

Although the invention has been shown and described with respect to preferred embodiments thereof, it should be understood by those skilled in the art that various changes, omissions and additions in the form and detail thereof may be made thereto and therein without departing from the spirit and scope of the invention.

Having thus described typical embodiments of my invention, that which I claim as new and desire to secure by Letters Patent of the United States is:

1. A reservoir means for a cryosurgical instrument comprising a metal vacuum bottle having an inner wall structure with a mouth forming a container for holding liquified gas cryogen and an outer wall structure separated from said inner wall structure except at a peripheral metallurgical joint between said outer and inner wall structures near the mouth of said inner wall structure, said wall structures thereby confining an insulating space between them, said space being at least partially evacuated through an aperture, in said outer wall structure at an end thereof opposite to said peripheral metallurgical joint, which is closed off upon evacuation so as to form a vacuum seal, and a pan encompassing the bottom of said outer wall structure, acting as a base for said vacuum bottle and protecting said vacuum seal, in which the improvement to render said reservoir means safer for containing a liquified gas cryogen in use in a cryosurgical instrument comprises:

a heavy metal collar metallurgically joined to said outer wall structure near the mouth of said inner wall structure so as to encompass said peripheral metallurgical joint, said collar having a thickness several times thicker than said wall structures; and a vent hole provided through said bottom pan to prevent the buildup of pressure therein, whereby said reservoir means is protected against rupture at said joint and expulsion of said pan as a consequence of cryogenic pressures in said insulating space which could result from a leak in said internal wall structure.

2. A cryosurgical instrument having application means for cryosurgical extraction of heat from living tissue in the treatment thereof, a reservoir means comprising a metal vacuum bottle having an inner wall structure with a mouth forming a container for holding liquid gas cryogen and an outer wall structure separated from said inner wall structure except at a peripheral metallurgical joint between said outer and inner wall structures, said wall structures thereby confining an insulating space between them, said space being at least partially evacuated, and operator-controlled means for conveying the cryogen from said reservoir means to said application means, in which the improvement comprises:

a heavy metal collar metallurgical joined to said outer wall structure near the mouth of said inner wall structure so as to encompass said peripheral metallurgical joint, said collar having a thickness several times thicker than said wall structures, said collar having external threads machined into the periphery thereof; and a cap having internal threads therein for engagement with the threads of said collar, said application means and said operator controlled means being disposed on said cap to provide an integral control and delivery portion which is releasably engageable to said reservoir means, whereby said reservoir means is reinforced against rupture by cryogenic pressure within said insulating space and said control and delivery portion is securely held to said reservoir means against cryogenic pressure in said container.

3. A cryosurgical instrument according to claim 2 wherein said vacuum bottle includes a vacuum seal extending from the end of said outer wall structure opposite to said joint and closed off upon evacuation of said insulating space and a pan encompassing the bottom of said outer wall structure, acting as a base for said vacuum bottle and protecting said vacuum seal, and the improvement further comprises:

a vent hole provided through said bottom pan to prevent the buildup of pressure therein, whereby said reservoir means is protected against rupture at said joint and expulsion of said pan as a consequence of cryogenic pressures in said insulating space which could result from a leak in said internal wall structure.

* * * * *